United States Patent [19]

Stone et al.

[11] Patent Number: 5,478,345
[45] Date of Patent: Dec. 26, 1995

[54] MECHANISM FOR ENDOSCOPIC SUTURING DEVICE

[75] Inventors: Corbett W. Stone, Newtown, Conn.; Stephen W. Zlock, Hawthorne, N.Y.; David Farascioni, Bethel, Conn.

[73] Assignee: United States Surgical Corporation, Norwalk, Conn.

[21] Appl. No.: 293,234

[22] Filed: Aug. 19, 1994

[51] Int. Cl.⁶ .................................................. A61B 17/04
[52] U.S. Cl. .......................... 606/144; 206/63.3; 206/339; 206/340; 206/438; 221/113; 221/119; 221/191; 222/144
[58] Field of Search ............. 606/144; 221/113, 221/119–122, 133; 206/338–341, 63.3, 438, 382; 222/144

[56] References Cited

U.S. PATENT DOCUMENTS

| | | |
|---|---|---|
| 3,456,817 | 7/1969 | Irazoqui . |
| 3,613,901 | 10/1971 | Montelius . |
| 3,901,244 | 8/1975 | Schweizer .................................. 221/2 |
| 4,084,692 | 4/1978 | Bilweis ...................................... 206/403 |
| 4,116,333 | 9/1978 | Pavel ......................................... 206/380 |
| 4,135,623 | 1/1979 | Thyen ........................................ 206/63.3 |
| 4,183,431 | 1/1980 | Schmidt et al. ........................... 206/63.3 |
| 4,418,821 | 12/1983 | Sandel ....................................... 206/63.3 |
| 4,424,898 | 1/1984 | Thyen et al. .............................. 206/63.3 |
| 4,449,630 | 5/1984 | Filhol ........................................ 206/369 |
| 4,496,045 | 1/1985 | Ferguson ................................... 206/476 |
| 4,524,891 | 6/1985 | Silva ......................................... 206/382 |
| 4,821,878 | 4/1989 | Jones ......................................... 206/370 |
| 5,056,658 | 10/1991 | Sobel ......................................... 206/63.3 |
| 5,078,730 | 1/1992 | Li et al. .................................... 606/228 |
| 5,152,422 | 10/1992 | Springer ................................... 206/63.3 |
| 5,199,565 | 4/1993 | Voroba ...................................... 206/333 |
| 5,226,536 | 7/1993 | Elliot ......................................... 206/369 |
| 5,271,495 | 12/1993 | Alper ........................................ 206/63.3 |

FOREIGN PATENT DOCUMENTS

| | | | |
|---|---|---|---|
| 0647431 | 10/1994 | European Pat. Off. . | |
| 2260704 | 4/1993 | United Kingdom ................... | 606/144 |

*Primary Examiner*—Gary Jackson

[57] ABSTRACT

A loading unit is disclosed for supplying multiple surgical needles or surgical incision members and associated lengths of suture material for positioning the needle or surgical incision member within the jaws of a surgical suturing apparatus. The loading unit generally includes a body portion having apparatus receiving structure for receipt of the surgical suturing apparatus and a carousel rotatably affixed to the body portion and containing a plurality of supply stations thereon. The supply stations generally include a support member for supporting a central portion of a surgical needle and a storage member for temporarily securing a length of suture material associated with the surgical needle. The apparatus receiving structure includes structure for aligning and maintaining the surgical suturing apparatus in position on the loading unit until such time as a surgical incision member has been inserted into jaws associated with the surgical suturing apparatus. Preferably, the apparatus receiving structure includes structure for gasping an elongate portion of the surgical suturing apparatus and structure for supporting jaw members associated with the surgical suturing apparatus. Additionally, in a preferred embodiment, the suture storage members consist of a suture reel which is positioned in a plane offset from the needle support members.

22 Claims, 7 Drawing Sheets

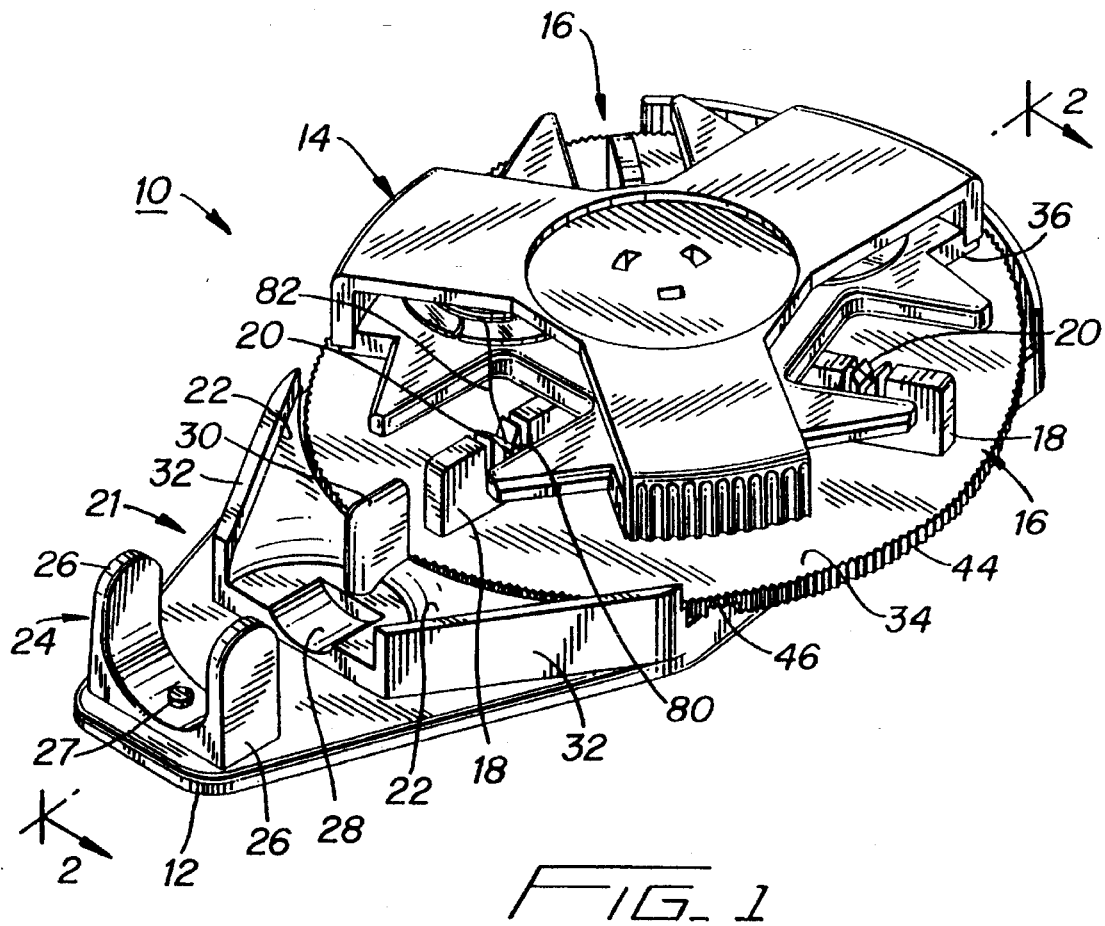
FIG_1
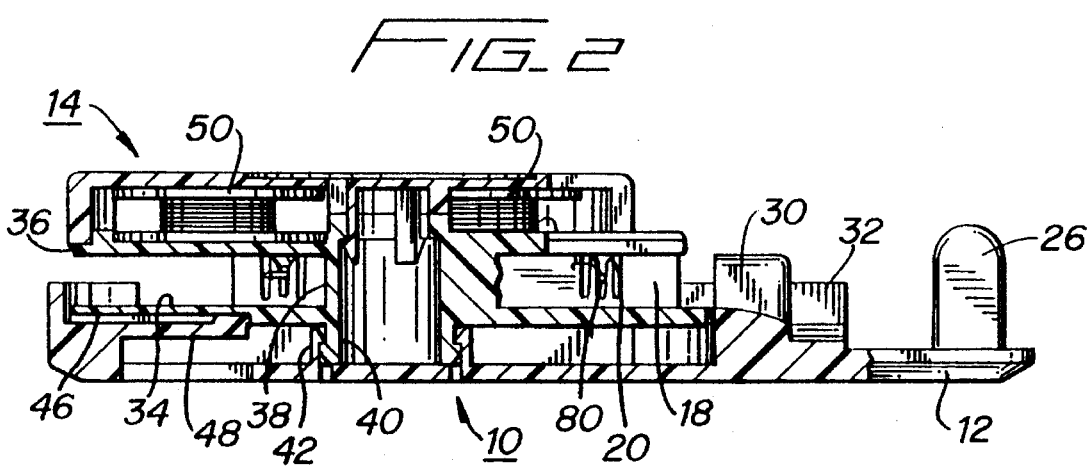
FIG_2

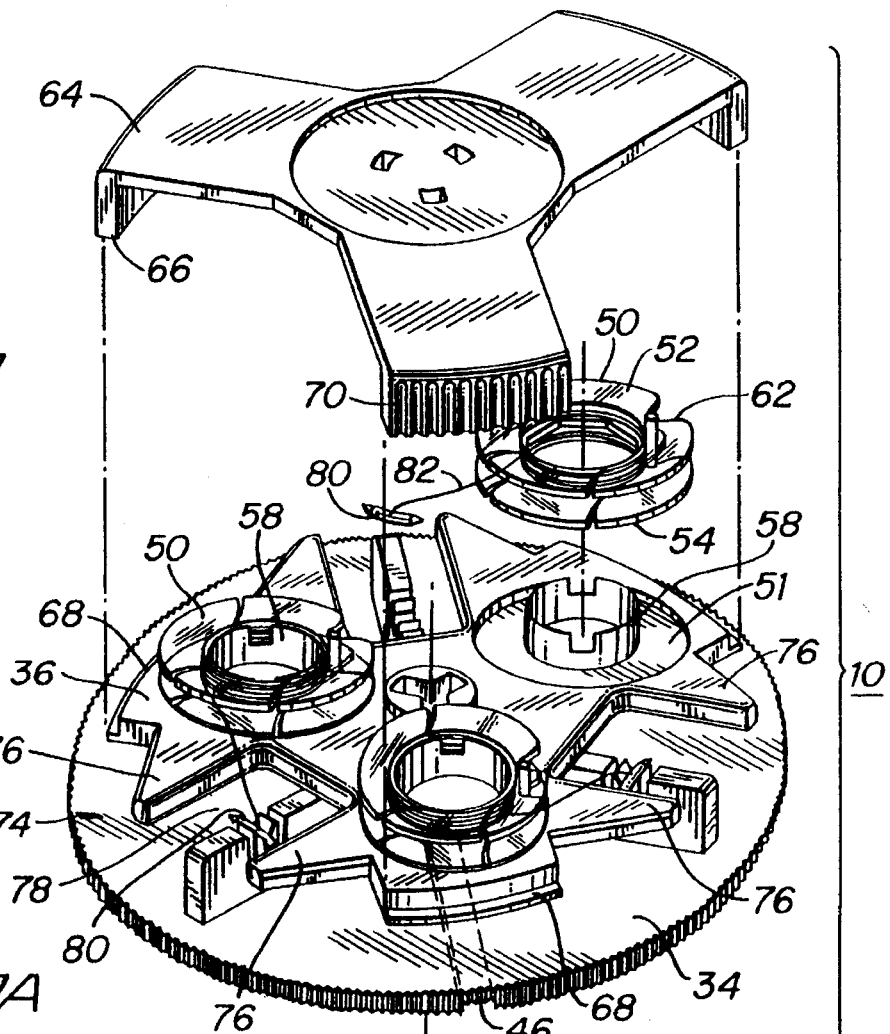
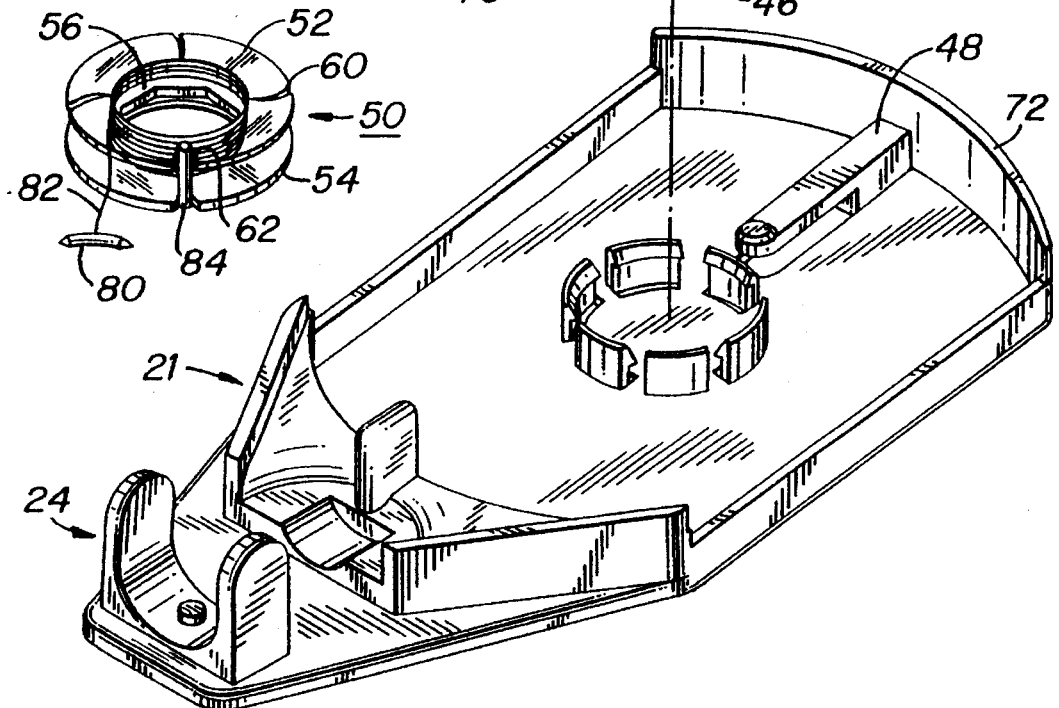

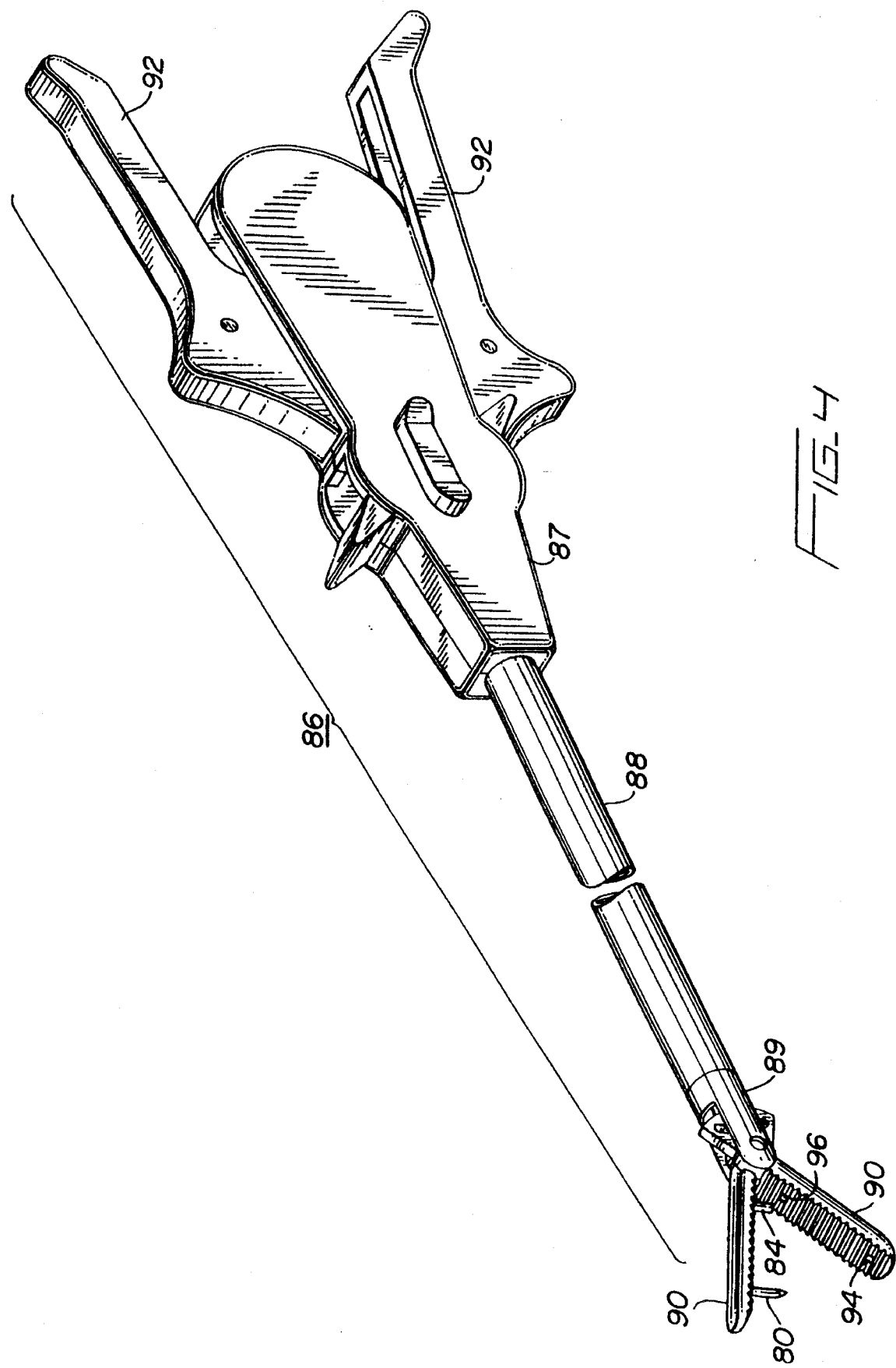

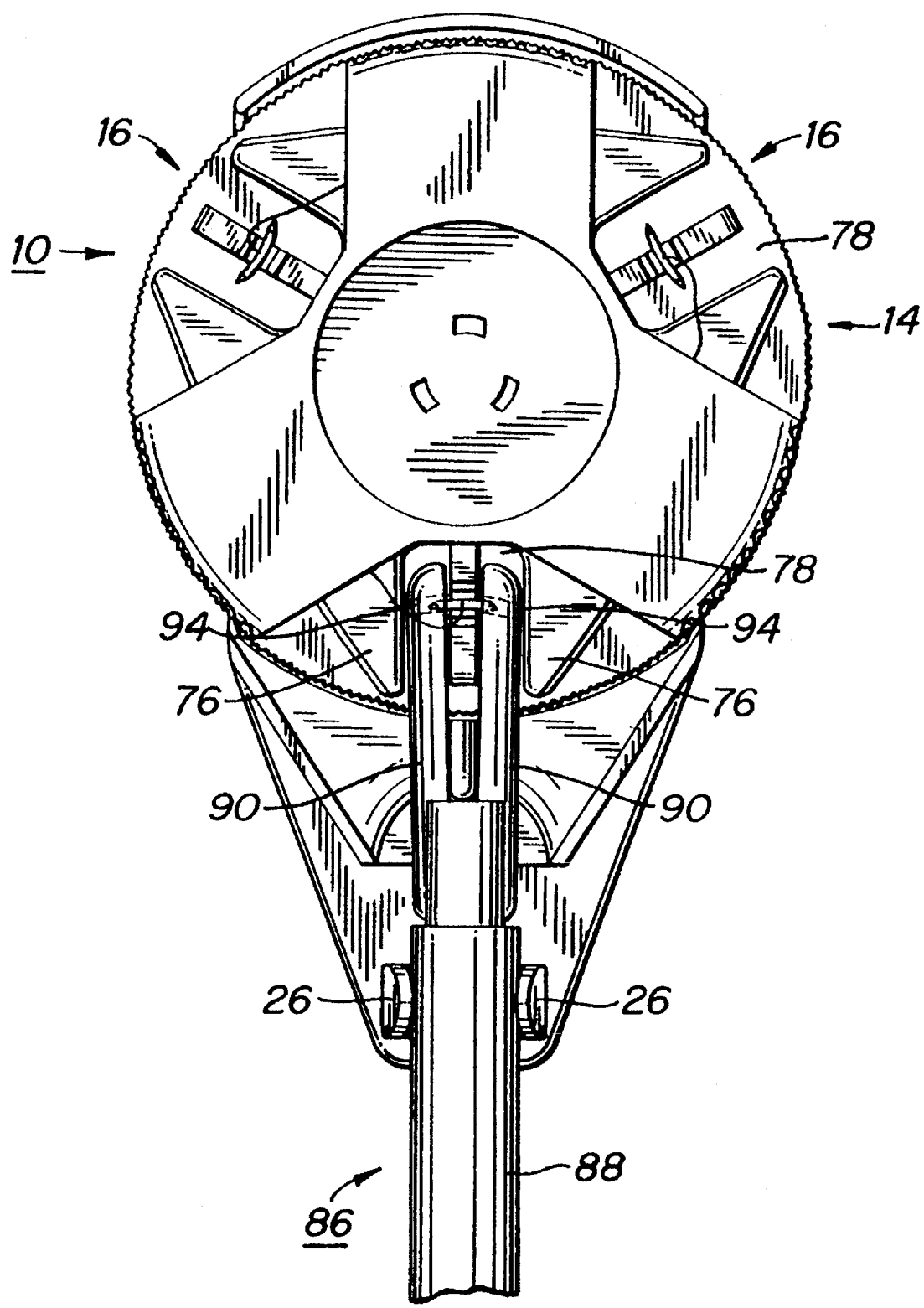

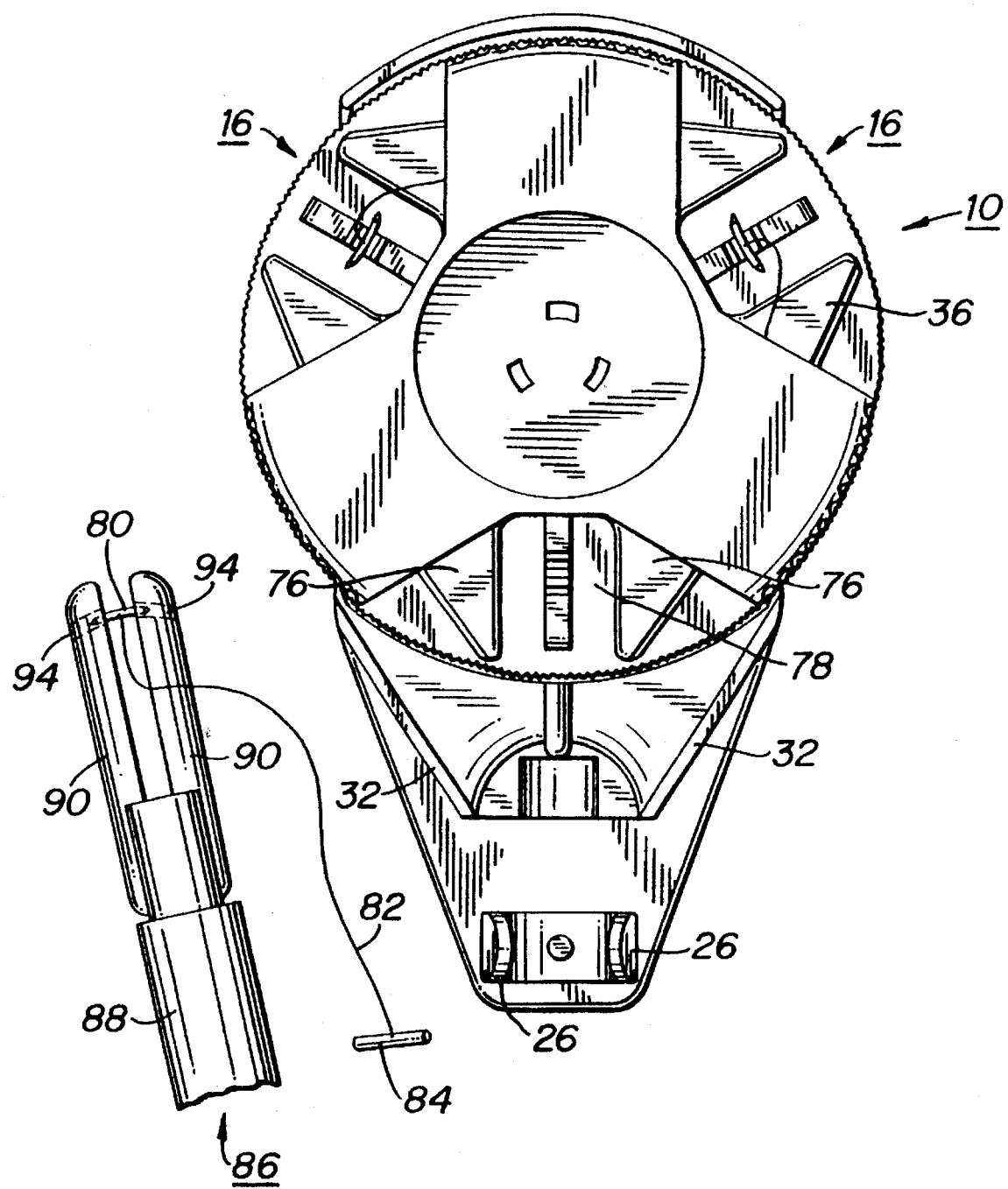

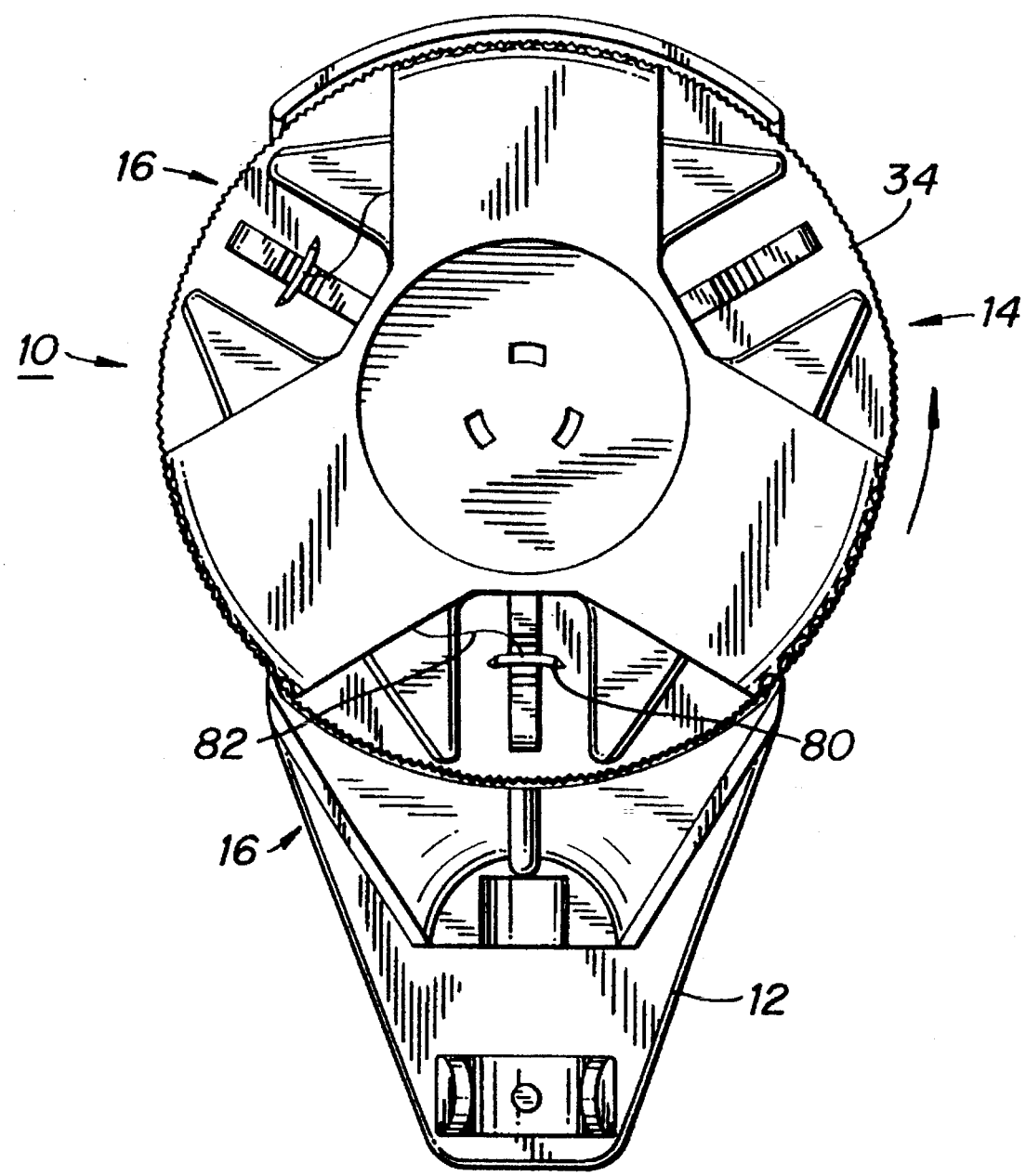
FIG_8

MECHANISM FOR ENDOSCOPIC SUTURING DEVICE

BACKGROUND

1. Technical Field

The device relates generally to surgical instrumentation and, more particularly, to a loading unit for supplying a plurality of surgical needles and; associated sutures to a surgical suturing apparatus.

2. Description of Related Art

Various types and styles of suture packages have been developed to hold surgical needles and associated length of suture for use during a surgical operation. These devices typically include a folded pouch containing a single needle and suture combination. To access the needle and suture, the package is unfolded and the needle/suture is removed by hand. During many surgical procedures, it is generally considered desirable to place two or three lines of stitching in tissue sections, such as, for example, to provide reinforcement when performing an anastomosis. A device for holding a plurality of sutures and needles is disclosed in U.S. Pat. No. 4,185,636 to Gabbay et al. Gabbay et al. disclose annular organizer members for holding multiple sutures each having a needle attached at one end thereof. Another device for holding several needles and sutures is disclosed in U.S. Pat. No. 4,424,898 to Thyen et at. The device of Thyen et al. includes a plurality of holders for surgical needles and a channel around the outer perimeter of the device to hold the sutures associated with the needles.

In using these various suture packages, it is often necessary to manually remove the needle/suture combination by hand and insert them into a surgical suturing apparatus. A dispenser for holding surgical needles and anchors is disclosed in U.S. Pat. No. 4,821,878 to Jones. The Jones dispenser is configured to hold the needle anchor in a position to be grasped by a manipulating tool.

Many surgical procedures call for placing stitches through tissue, a procedure traditionally accomplished by hand. It is desirable to remotely join tissue together by passing a needle, having a length of suture material attached thereto, back and forth between jaws located on opposite sides of the tissues. One such device is disclosed in U.S. Pat. No. 4,236,470 to Stenson. Stenson discloses a skin-stitching instrument that includes a pair of arms configured to alternately receive opposed ends of a shuttle needle. The shuttle needle with an attached length of filament is passed alternately back and forth between the arms to remotely stitch tissue together.

Laparoscopic suturing presents an even greater challenge because it must be accomplished through a port that typically averages between five and ten millimeters. One instrument for facilitating laparoscopic suturing is discussed in British Patent Application No. 2260704, published Apr. 28, 1993.

Although the suturing device described in British Patent Application Serial No. 2260704 can be used to place laparoscopic sutures, once the suture is used up, or if a new needle is required, the suturing device must be manually re-loaded, which can be time-consuming. As it is generally considered desirable to place 2 or 3 lines of stitching when performing an anastomosis to provide reinforcement, the laparoscopic suturing device as described in the British Patent Application mentioned above requires manual reloading one or more times.

Thus, during many endoscopic procedures, it is necessary to rapidly and accurately place successive needle-suture combinations within the jaws of a surgical suturing apparatus for immediate and repeated use during the surgical procedure. Further, it is often necessary to grasp the needles at specific locations along the needle body to facilitate suturing such as, for example, at one end or the other. Thus, it is desirable to have a needle and suture supplying device which is capable of supplying a plurality of needles and positioning them within the jaws of a surgical suturing apparatus. It is also desirable to have an apparatus receiving structure associated with the device for receipt of a surgical suturing apparatus and to guide the apparatus into position for precisely grasping opposing ends of a needle such as, for example, a double ended surgical incision member, between the jaws of the suturing apparatus.

SUMMARY

The disclosed surgical instrument relates to a loading unit for positioning and assisting in positioning a surgical needle in the jaws of a surgical suturing apparatus. The loading unit generally includes a body portion having apparatus receiving structure and a carousel rotatably affixed to the body portion for successively positioning a series of supply stations in alignment with the apparatus receiving structure. Preferably the apparatus receiving structure includes a pair of tabs configured to engage an elongate portion of the surgical suturing apparatus and a pair of support shelves to support jaw portions of the surgical suturing apparatus adjacent the supply stations. The supply stations include a support member having a retaining notch therein and an associated storage member for storing a length of suture material associated with each needle. The suture storage members are preferably suture reels rotatably affixed to the carousel and positioned in a plane offset from the supporting member. An indexing structure may be provided to temporarily lock in the supply stations adjacent the apparatus receiving structure.

The loading unit may additionally include a safety feature in the form of a pair of blocking members which prevent withdrawal of the surgical suturing apparatus from the loading unit until such time as the surgical needle has been fully grasped by the jaws of the surgical suturing apparatus.

In one embodiment of the suture reels, the reels are provided with recesses for releasably holding a suture anchor associated with a length of suture material.

Also disclosed is a method of successively supplying surgical incision members and associated lengths of suture material to a surgical suturing apparatus. The method includes the steps of providing a loading unit of the type described hereinabove and aligning a needle or surgical incision member supply station adjacent the apparatus receiving structure. A distal end of a surgical suturing apparatus is positioned within the apparatus receiving structure such that jaws associated with the surgical suturing apparatus are positioned adjacent the support member and thus adjacent the surgical needle or surgical incision member. Closing the jaws of the surgical suturing apparatus causes the needle or surgical incision member to be positioned in recesses of the jaws. Finally, the needle or surgical incision member and associated length of suture material are pulled free of their respective mounting members and storage members to release the needle or surgical incision member and suture material from the loading unit. The method may additionally include the further step of rotating the carousel with respect to the body portion to position a next loaded supply station in alignment with the apparatus receiving structure to again load a needle or surgical incision member and associated length of suture material within the jaws of a surgical suturing apparatus. As used herein, "needle" or "surgical needle" refers generically to all types of surgical needles while "surgical incision member" is directed to double pointed needles for use with a surgical suturing apparatus. Because the loading unit is particularly suited for loading a surgical incision member within the jaws of a surgical suturing apparatus, the term surgical incision member will be used herein. However, it will be understood that a surgical needle may be used in place of the surgical incision member.

BRIEF DESCRIPTION OF THE DRAWINGS

Various embodiments are described herein with reference to the drawings, wherein:

FIG. 1 is a perspective view of a preferred embodiment of a loading unit;

FIG. 2 is a side elevational view of the loading unit, partly shown in section, taken along the lines 2—2 of FIG. 1;

FIG. 3 is an exploded perspective view of the loading unit of FIG. 1;

FIG. 3A is a perspective view of a suture reel and associated suture, surgical incision member and suture anchor suitable for use with the loading unit of FIG. 1;

FIG. 4 is a perspective view of a surgical suturing apparatus;

FIG. 6 is a view similar to FIG. 5 with the jaws of the surgical suturing apparatus in a closed position;

FIG. 7 is a view similar to FIG. 6 illustrating a surgical incision member and associated suture and suture anchor being removed from the loading unit; and FIG. 8 is a view similar to FIG. 5 illustrating the carousel being rotated to present a loaded supply station to the apparatus receiving structure.

DETAILED DESCRIPTION OF PREFERRED EMBODIMENTS

Figure 5:
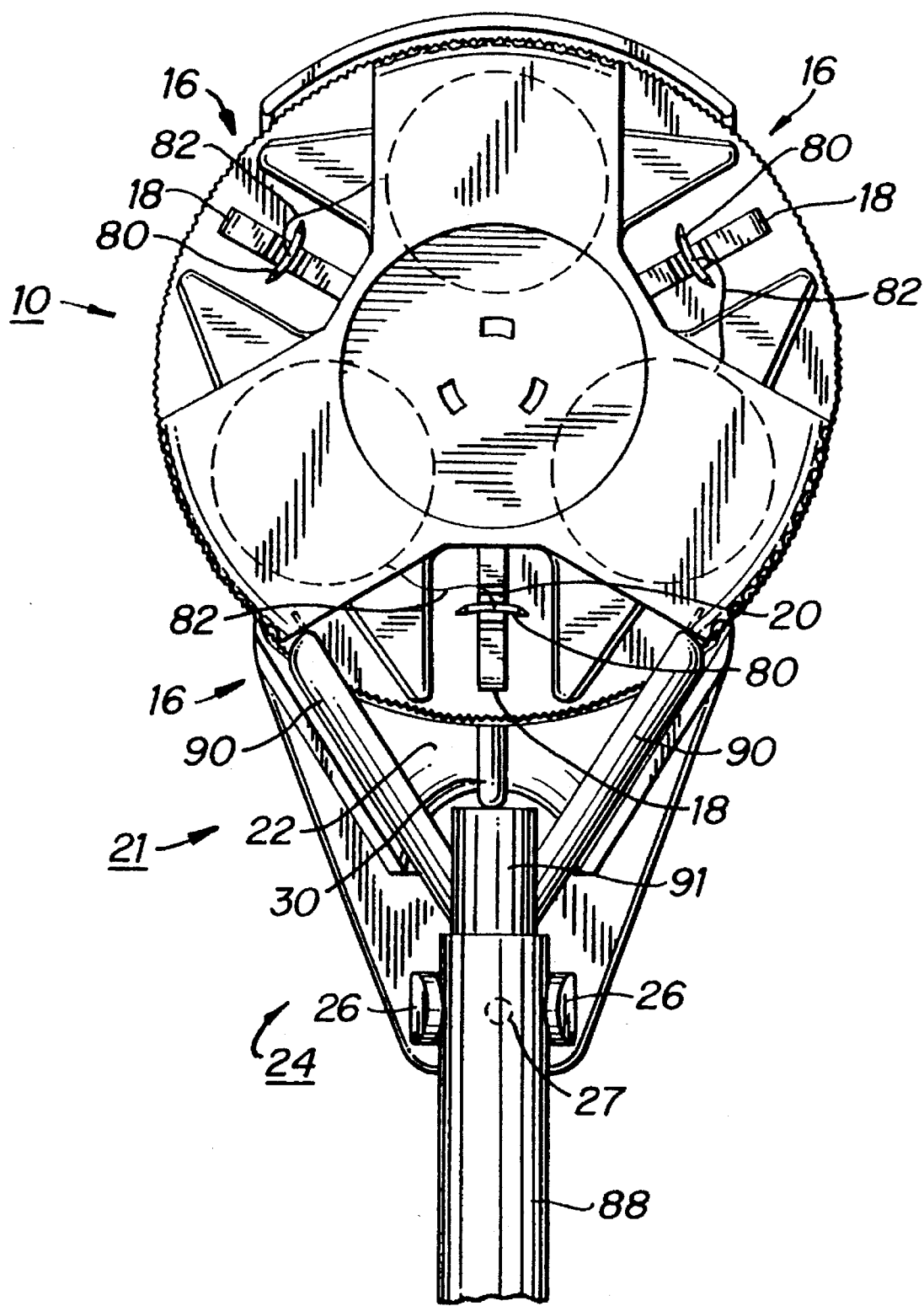
FIG. 5 is a top plan view of the loading unit of FIG. 1 illustrating the surgical suturing apparatus positioned thereon with the jaws in an open position.

Referring to FIGS. 1–3A, there is disclosed a loading unit 10 suitable for use with a surgical suturing apparatus. Loading unit 10 is provided to rapidly and positively seat a surgical needle or incision member and associated suture such as, for example, surgical incision member 80 and associated suture 82, within the jaws of the surgical suturing apparatus. Loading unit 10 is particularly suitable for providing a plurality of surgical incision members 80 and associated sutures 82 for use with the surgical suturing apparatus.

Referring now to FIGS. 1 and 2, loading unit 10 generally includes a body portion 12 having a carousel 14 rotatably affixed thereon. Carousel 14 is provided with a plurality of supply stations 16, each having a surgical incision member support member 18. A notch 20 in each of support members 18 is provided to securely and releasably support a surgical incision member within each supply station. While the preferred embodiment of loading unit 10 is illustrated with three surgical incision member supply stations 16 on carousel 14, it is within the contemplated scope of the appended claims to provide varying numbers of supply stations on carousel 14 depending on the type of surgery and number of suture combinations required. Loading unit 10 is specifically configured to receive, and hold in alignment, a surgical suturing apparatus for receipt of a surgical incision member. Body portion 12 has surgical apparatus receiving structure 21 formed thereon which generally includes a pair of jaw support shelves 22 configured to support jaw portions of a surgical suturing apparatus about support members 18. An elongate member alignment structure 24 is provided and is configured to grasp an elongate portion of the surgical suturing apparatus. Alignment structure 24 generally includes a pair of side tabs 26 which surround the elongate portion of the suture apparatus. A support stud 27 may be provided on a bottom edge of alignment structure 24 to maintain the elongate portion in proper vertical alignment when aligned with recess 100 located at the distal end of the elongated portion of the suturing apparatus shown in FIG. 4. Further, a recess, such as for example, recess or cup 28, may be provided between jaw support shelves 22 to support the distal end of the elongate portion. When inserted in alignment structure 24, the distal end of the surgical suturing apparatus elongate portion will engage an abutment member 30 to limit advancement of the jaws within loading unit 10. Additionally, a pair of side walls 32 are provided adjacent each side of jaw support shelves 22 to guide the jaws into position about needle support member 18. Side walls 32 are provided on jaw support shelves 22 and generally taper towards cup 28. Side walls 32 aid in ensuring consistent horizontal alignment of the jaws on support shelves 22 and additionally aid in preventing premature withdrawal of the suturing apparatus out of loading unit 10.

As noted hereinabove, carousel 14 is provided to successively present supply stations 16 to apparatus receiving structure 21. Carousel 14 includes a lower plate 34 upon which support members 18 are mounted. Carousel 14 further includes an upper plate 36, positioned above support members 18, which is connected to the lower plate 34 by means of a central hub 38. Referring to FIG. 2, male portions or prongs 40 formed on central hub 38 engage corresponding female portions 42 formed on body portion 12. The engagement of male and female portions 40 and 42, respectively, enables carousel 14 to rotate with respect to body portion 12. Knurling, such as ridges 44, are preferably formed in an outer edge of lower plate 34 to facilitate rotation of carousel 14 by the fingers of the user. Thus, carousel 14 presents successive supply stations 16 to apparatus receiving structure 21 by rotating carousel 14 with respect to body portion 12.

Supply stations 16 are movable from a remote position spaced from apparatus receiving structure 21 to an aligned position adjacent apparatus receiving structure 21. As carousel 14 is rotated with respect to body portion 12, an indexing mechanism is provided to align and temporarily "lock in" a supply station 16 and thus a support member 18 adjacent to apparatus receiving structure 21. As best seen in FIGS. 2 and 3, the indexing mechanism includes an index detent 46 formed on an underside of lower plate 34 which engages the flexible index finger 48 formed on body portion 12. Preferably, there are indexing detents 46 associated with each supply station 16 and are located on carousel 14 diametrically opposite each support member 18 so that the user feels a "click" when a supply station 16 becomes properly aligned with a receiving structure 21. While index detent 46 and index finger 48 are positioned opposite support member 18 and abutment 30, respectively, it will be obvious to one skilled in the art that index detent 46 and index finger 48 may be positioned at various other corresponding and predetermined locations to ensure consistent alignment of supply station 16 with apparatus receiving structure 21. Lower plate 34 and supply station 16 preferably remain stationary to each other, rotating as a unit with respect to body portion 12.

As noted hereinabove, surgical incision member 80 is preferably provided with a length of suture material 82. It is desirable to maintain a length of suture material 82 in orderly and secure fashion until such time as surgical incision member 80 is removed from loading unit 10. Referring now to FIGS. 2 and 3, it can be seen that loading unit 10 is provided with a storage mechanism for releasably securing a length of suture 82 on loading unit 10. Preferably, the storage mechanism includes a plurality of suture reels 50 positioned in recesses 51 formed in upper plate 36. A single suture reel 50 is associated with each supply station 16 to secure the suture 82 associated with each surgical incision member 80. Referring to FIGS. 3 and 3a, suture reels 50 generally include an upper portion 52 and a lower portion 54 connected by a center portion 56. Suture reels 50 are preferably rotatably mounted on upper plate 36 by means of reel guides 58 positioned within recesses 51 and which engage the inner surfaces of center portions 56. In order to ensure against inadvertent unraveling of suture material 82, upper and lower portions 52, 54, respectively, of suture reel 50 may be provided with suture slot 60 around the circumference thereof to wedge suture 82. Additionally, a suture anchor slot 62 may be provided in upper and lower portions 52, 54, respectively, to hold a suture anchor 84 associated with suture 82.

A suture reel cover 64 is provided to engage carousel 14 and hold suture reels 50 in position on reel guides 58. Preferably, edges 66 of suture reel cover 64 overlap recessed edges 68 of upper plate 36. Edges 66 may also be adapted to snap on to upper plate 36. Additionally, a plurality of male prongs (not shown) similar to prongs 40 engage a corresponding female portions of upper plate 36 similar to female portion 42 in order to secure cover 64 to upper plate 36. Knurling 70 may be formed in outer edge of cover 64 to facilitate rotation of carousel 14.

A back wall 72 is formed in body portion 12 and generally conforms to the outer circumference of carousel 14. Back wall 72 is provided to assist the user in firmly grasping loading unit 10 without causing inadvertent rotation of carousel 14.

Various structure or safety features may be provided to ensure that surgical incision member 80 may not be removed from loading unit 10 until surgical incision member 80 has been firmly gasped by the jaws of the surgical suturing instrument. A safety mechanism 74 is provided to prevent lifting of the jaws, and thus lifting of surgical incision member 80, out of loading unit 10 before it has been firmly grasped by the jaws. Safety mechanism 74 generally includes a pair of triangular blocking members 76 formed in upper plate 36 and which are positioned above and adjacent either side of support member 18. Blocking members 76 prevent vertical movement of the jaws out of loading unit 10 until the jaws are closed. Once the jaws of a surgical suturing apparatus have been firmly and positively closed about surgical incision member 80, the jaws may be lifted vertically through a gap 78 located between blocking members 76 in order to remove surgical incision member 80 from loading unit 10. Thus, members 76 in conjunction with side walls 32 aid in ensuring that a surgical incision member 80 is not removed from loading unit 10 until jaws have been fully closed and firmly grasp the surgical incision member.

Loading unit 10 may be formed of any suitable material such as, for example polycarbonate or other medical plastic. Suture reel 50 may also be formed of any suitable material such as, for example polyethylene. Additionally, various labeling methods may be employed at various positions on loading unit 10 to indicate the size and type of needle and suture loaded in unit 10 or the type of suturing apparatus to be used therewith.

As discussed hereinabove, loading unit 10 is configured to supply a plurality of surgical incision members 80 and associated sutures 82 and to rapidly and positively load the surgical incision members and sutures 82 into the jaws of a surgical suturing apparatus. A particularly suitable suturing apparatus for use with loading unit 10 is disclosed in U.S. patent application Ser. No. 08/134,145 entitled "SURGICAL SUTURING APPARATUS WITH LOADING MECHANISM", the disclosure of which is incorporated by reference herein.

Referring to FIG. 4, suturing apparatus 86 generally includes a body portion 87 having an elongate portion 88 extending distally thereof. A pair of pivotally movable jaws 90 are provided at a distal end 91 of elongate portion 88 and serve to grasp surgical incision member 80 within needle holding recesses 92 in each of the jaws 90. Handles 92 are preferably pivotably mounted with respect to body portion 87 and serve to open and close the jaws as more fully described in U.S. patent application Ser. No. 08/134,145. Additionally, a suture anchor recess 96 may be provided to hold suture anchor 84 and, as described above, recess 100 may aid in proper alignment of the suturing and loading mechanisms.

Referring now to FIGS. 5–8, and initially to FIG. 5, surgical incision members 80 are initially placed on support members 18 and supported in holding notches 20. Sutures 82 extend from a central portion of each surgical incision member 80 and are wound around suture reels 50. Initially, each supply station 16 is so loaded with a surgical incision member 80 and associated length of suture material 82. In use, the user firmly grasps loading unit 10 and rotates carousel 14 until index finger 48 snaps into an index detent 46. As noted hereinabove, index finger 48 and index detent 46 maintains a supply station 16 in proper alignment with apparatus receiving structure 21. Surgical suturing apparatus 86 is then inserted into loading unit 10 with jaws 90 in an open position by positioning elongate member portion 88 between side tabs 26 and by aligning recess 100 on the suturing apparatus with stud 27 on the loading mechanism. Stud 27 aids in ensuring consistent vertical alignment of jaw recesses 92 with the ends of surgical incision member 80. Distal end 89 of elongate member 88 contacts abutment 30 to limit the degree to which suturing apparatus 86 is inserted into loading unit 10. When positioned in loading unit 10, jaws 90 are initially placed in an open condition on jaw support shelves 22.

Referring now to FIG. 6, once suturing apparatus 86 has been positioned on loading unit 10, jaws 90 are pivoted to a closed position, in a manner more fully described in U.S. patent application Ser. No. 08/134,145, such that recesses 94 surround and firmly grasp the ends of surgical incision number 80. As most clearly shown in FIG. 7, suturing apparatus 86 may now be lifted vertically through gap 78 between blocking members 76, removing elongate portion 88 from side tabs 26.

As discussed hereinabove, safety mechanism 74 helps prevent suturing apparatus 86 from being removed from loading unit 10 until jaws 90 have been fully closed about surgical incision member 80. For example, should jaws 90 only be partially closed towards surgical incision member 80, jaws 90 will be blocked by members 76 and will be unable to pass through gap 78. If only partially closed, suturing apparatus 86 cannot be removed from loading unit 10 in a vertical direction. Further, should the user attempt to draw suturing apparatus 86 out of loading unit 10 in a longitudinal direction, partially open jaws 90 will cam against side walls 32 preventing further longitudinal withdrawal of suturing apparatus 86. Thus, in this fashion, loading unit 10 is particularly suited to ensure that a surgical incision member 80 is positively seated within jaws 90 of suturing apparatus 86 prior to removal of surgical incision member 80 from loading unit 10. This has the advantage of helping prevent surgical incision member 80 from falling out of jaws 90 due to incomplete positioning or partial securement of the incision member within the jaws.

Referring to FIG. 7, as surgical incision member 80 is pulled free of loading unit 10, suture 82 attached thereto is caused to unravel from suture reel 50 as suture reel 50 rotates with respect to upper plate 36. In this manner, loading unit 10 enables a user to rapidly and positively seat surgical incision member 80 within jaws 90 of surgical suturing apparatus 86 while maintaining a suture 82 in a secure condition until such time as surgical incision member 80 is pulled free of loading unit 10. Suturing apparatus 86 is now in a "loaded condition" containing surgical incision member 80 and associated suture 82 and, in an alternate embodiment, a suture anchor 84 attached to suture 82, and is ready to be used in a surgical operation.

Referring now to FIG. 8, once surgical incision member 80 and suture 82 have been removed from support member 18 and suture reel 50, respectively, carousel 14 may be rotated with respect to body portion 12 until index finger 48 again engages index detent 46 to thereby present a "loaded" supply station 16 to apparatus receiving structure 22. In this manner, loading unit 10 is particularly suited to successively supply surgical incision members 80 and associated sutures 82 to a position on loading unit 10 for receipt by surgical suturing instrument jaws 90. The entire loading unit 10 preferably is packaged sterile in appropriate packaging for a given suture material.

It will be understood that various modifications may be made to the embodiments disclosed herein. For example, surgical needles may be substituted for the surgical incision members and four or more loading stations may be incorporated in the carousel. Therefore, the above description should not be construed as limiting, but merely as exemplifications of preferred embodiments. Those skilled in the art will envision other modifications within the scope and spirit of the claims appended hereto.

What is claimed is:

1. A loading unit for supplying a plurality of surgical needles to a surgical suturing apparatus comprising:
 a) a body portion having apparatus receiving structure formed thereon; and
 b) at least one supply station configured to hold a surgical needle and movably mounted with respect to the body portion, the at least one supply station mounted for movement between a first position adjacent the apparatus receiving structure and a second position remote from the apparatus receiving structure.

2. The loading unit as recited in claim 1, wherein the at least one supply station is positioned on a carousel rotatably affixed to the body portion.

3. The loading unit as recited in claim 2, further comprising indexing structure connected to the carousel and the body portion to frictionally maintain the at least one supply station in alignment with the apparatus receiving structure.

4. The loading unit as recited in claim 3, wherein said index structure includes a portion of the carousel defining a detent therein and a flexible finger formed on the body portion and positioned to engage the detent when the supply station is correctly aligned with the apparatus receiving structure.

5. The loading unit as recited in claim 2, wherein the carousel includes three supply stations.

6. The loading unit as recited in claim 1, wherein the apparatus receiving structure includes a pair of tabs formed on the body portion for receipt of an elongate portion of the surgical suturing apparatus and an abutment structure also formed on the body portion to engage a distal end of the elongate portion, the pair of tabs and abutment structure aligning jaws associated with the distal end of the elongate portion about the surgical needle.

7. The loading unit as recited in claim 1, wherein the apparatus receiving structure includes a pair of walls formed on the body portion and defining a recess there between for receipt and support of a pair of jaws associated with the distal end portion of the surgical suturing apparatus.

8. The loading unit as recited in claim 1, wherein the at least one supply station includes a mounting member for releasably supporting the surgical needle by a central portion thereof.

9. The loading unit as recited in claim 8, wherein the at least one supply station further includes a storage member for holding a portion of a length of suture material affixed to the surgical needle.

10. The loading unit as recited in claim 9, wherein the storage member is a suture reel rotatably affixed to the carousel.

11. The loading unit as recited in claim 10, wherein the mounting member is in a first plane on the carousel and the suture reel is located in a second plane on the carousel offset from the first plane.

12. The loading unit as recited in claim 11, wherein the first plane is vertically offset with respect to the second plane.

13. The loading unit as recited in claim 11, wherein the suture reel includes structure to releasably hold a suture anchor associated with the length of suture material.

14. The loading unit as recited in claim 8, further comprising a safety mechanism including a pair of blocking members disposed adjacent the mounting member, the blocking members preventing vertical removal of jaws associated with the surgical suturing apparatus from the supply station until the surgical needle has been fully grasped by the jaws.

15. The loading unit as recited in claim 1, wherein the surgical needle is a surgical incision member.

16. A loading unit for supplying multiple surgical needles and each connected to a length suture to a surgical suturing apparatus comprising:
 a) a body portion having apparatus receiving structure for receipt of at least a portion of a surgical suturing apparatus;
 b) a carousel rotatably affixed to the body portion; and
 c) a plurality of supply stations on the carousel.

17. The loading unit as recited in claim 16, wherein the supply stations include a mounting member for releasably supporting a central portion of a surgical needle and a storage member for temporarily securing a portion of a length of suture associated with the surgical needle.

18. The loading unit as recited in claim 17, wherein the storage member is a suture reel rotatably affixed to the carousel.

19. The loading unit as recited in claim 16, further comprising index structure associated with the body portion and carousel for temporarily maintaining one of the supply stations in alignment with the apparatus receiving structure.

20. The loading unit as recited in claim 16, wherein the surgical needle is a surgical incision member.

21. A method of successively supplying surgical needles to a surgical suturing apparatus comprising:

a) providing a loading unit having apparatus receiving structure on a body portion thereof and a carousel, containing a plurality of supply stations and rotatably mounted on the body portion, each supply station having a mounting member releasably supporting a surgical needle;

b) aligning a supply station adjacent the apparatus receiving structure;

c) positioning at least a distal end of a surgical suturing apparatus within the apparatus receiving structure such that jaws associated with the surgical suturing apparatus are positioned adjacent the mounting member;

d) closing the jaws to firmly grasp the surgical needle therebetween; and e) pulling the surgical needle free of the mounting member.

22. Method of claim 1 wherein the needle is a surgical incision member.

* * * * *